US011529418B2

(12) United States Patent
Guerret et al.

(10) Patent No.: US 11,529,418 B2
(45) Date of Patent: Dec. 20, 2022

(54) TEMPERATURE-CONTROLLED SEMIOCHEMICAL COMPOSITION DIFFUSERS

(71) Applicant: CEVA SANTE ANIMALE, Libourne (FR)

(72) Inventors: Olivier Guerret, Pern (FR); Samuel Dufour, Magny le Hongre (FR)

(73) Assignee: CEVA SANTE ANIMALE, Libourne (FR)

( * ) Notice: Subject to any disclaimer, the term of this patent is extended or adjusted under 35 U.S.C. 154(b) by 268 days.

(21) Appl. No.: 16/956,763

(22) PCT Filed: Dec. 21, 2018

(86) PCT No.: PCT/EP2018/086781
§ 371 (c)(1),
(2) Date: Jun. 22, 2020

(87) PCT Pub. No.: WO2019/122424
PCT Pub. Date: Jun. 27, 2019

(65) Prior Publication Data
US 2021/0052640 A1   Feb. 25, 2021

(30) Foreign Application Priority Data

Dec. 22, 2017 (EP) ..................... 17209898

(51) Int. Cl.
| A61K 47/32 | (2006.01) |
| A61K 9/00 | (2006.01) |
| A61K 35/12 | (2015.01) |
| A61K 47/06 | (2006.01) |
| A61K 47/34 | (2017.01) |

(52) U.S. Cl.
CPC .............. *A61K 47/32* (2013.01); *A61K 9/007* (2013.01); *A61K 35/12* (2013.01); *A61K 47/06* (2013.01); *A61K 47/34* (2013.01)

(58) Field of Classification Search
None
See application file for complete search history.

(56) References Cited

U.S. PATENT DOCUMENTS 10,058,526 B2 * 8/2018 Lacoste .................. A61K 31/20

FOREIGN PATENT DOCUMENTS

| EP | 2 926 809 | 10/2015 | |
| EP | 3 187 046 | 7/2017 | |
| EP | 3187046 A1 * | 7/2017 | ............. A01N 25/10 |

OTHER PUBLICATIONS

Solvay, Rhodiasolv Product Information sheet, accessed May 12, 2022 (Year: 2022).*
International Search Report and Written Opinion of the ISA for PCT/EP2018/086781 dated Feb. 28, 2019, 15 pages, along with English Translation of the International Search Report.
English Abstract of JPS57139005, published Aug. 27, 1982, Applicant, Otsuka Pharmaceutical Co., Ltd., title: "Controlled release pheromone paste preparation", Chemical Abstract, 1 page.

* cited by examiner

*Primary Examiner* — Melissa S Mercier
(74) *Attorney, Agent, or Firm* — Nixon & Vanderhye P.C.

(57) ABSTRACT

The present invention describes new formulations of semiochemical compounds for mammals in wick diffusers particularly effective in controlling the diffusion of several semiochemicals having different volatilities over long periods of time and independently of the temperature and humidity conditions.

11 Claims, No Drawings

TEMPERATURE-CONTROLLED SEMIOCHEMICAL COMPOSITION DIFFUSERS

This application is the U.S. national phase of International Application No. PCT/EP2018/086781 filed Dec. 21, 2018 which designated the U.S. and claims priority to EP Patent Application No. 17209898.0 filed Dec. 22, 2017, the entire contents of each of which are hereby incorporated by reference.

INTRODUCTION

The present invention describes new formulations of semiochemical compounds for mammals in wick diffusers that are particularly effective for controlling the diffusion of several semiochemicals having different volatilities over long periods of time and independently of temperature and humidity conditions.

The problem of appeasing animals, whether they are pets or livestock, is a significant problem which has been widely studied in the prior art. Indeed, the products used are of significant economic importance and owners have a need to combat unpleasant behavior and symptoms in domesticated animals, in particular dogs and/or cats, and, for livestock farmers, there is an economic importance in appeasing livestock animals in order to increase their productivity and their well-being.

Semiochemical compounds are chemical substances that are pure or in a mixture, and which are used by a large number of animal species to communicate. Semiochemicals are divided up into various categories depending on the nature of the emitter and the receptor. When the emitter and the receptor are individuals of one and the same species, the term used is pheromones. The terms pheromones and semiochemicals will be used interchangeably in this application.

From the beginning of the 1990s it has been shown that certain mammals, such as cats, dogs, pigs and horses, are sensitive to certain pheromones specific to each species. In general, these pheromones consist of a mixture of fatty acids or fatty esters having quite high boiling points.

Reference may be made to patents WO 2015/14063A1; WO 1996/023414A1; WO 1999/037297A1, WO 2004/000336A1 or GB 2345635 for the description of such pheromones and to understand their use.

The principle for the use of these pheromones consists in mimicking what the animals themselves do when they mark for example their territory. For example, the applicant has developed sprayers containing alcoholic solutions of pheromones which can be applied to any type of support. Once the alcohol has evaporated, the pheromones will remain on the support and will be detectable by the animal, which will then believe that it is in a marked territory and this will appease said animal.

Another example of application consists in using wick air-freshener diffusers. These diffusers consist of a bottle filled with a paraffinic solution of pheromones which elutes along the wick. The exterior portion of the wick is in an air gap heated by means of a resistance. The action of the heat on the wick dissipates the formulation in the premises. The pheromones are deposited on all the supports of the room, which has the effect of reassuring the animal that is in the room.

The paraffinic formulations used to date have mass concentrations of pheromones of about 2 to 5%. This means that 95 to 98% of the substance emitted into the room is a paraffin.

The importance of the choice of the paraffin, which must be absolutely neutral so as not to disturb the behavior of the animal, without mentioning drawbacks that can affect the perception of the product by the owner of the animal, is therefore understood.

In point of fact, recently, liquid paraffins have been categorized as toxic products in the event of pulmonary aspiration owing to their very low viscosity at low shear gradient. This implies that all products manufactured with said paraffins must be labeled, which affects the perception of the current wick diffusers.

Furthermore, in order to be effective, the pheromones must be diffused regularly over time, and this diffusion must not vary over time as a function of the temperature or the humidity in the environment in which they are diffused.

It is therefore important to find solutions to replace these paraffins.

The applicant has therefore sought to find solvents which exhibit the following collection of properties:
- solvent non-toxic (to humans or the environment)
- solvent having a boiling point>200° C. under atmospheric pressure
- solvent with no side effect for domestic use (no deterioration of wooden or plastic supports or coatings thereof)
- solvent compatible with mammalian pheromones
- solvent capable of diffusing according to the same characteristics as paraffins (temperature of wick bottle diffusers and materials).

Among the solvents which have at least the first 2 characteristics, the applicant has identified polyesters, such as Rhodiasolve™, or polyglycols, such as Dowanol™ or Solvenon™, or else such as 2-ethylhexylal and tetraoxaundecane.

None of these solvents meets all of these specifications. For example, polyesters are extremely polar and have a tendency to degrade plastics (PVC for example) which makes them incompatible with diffusion in a modern home. In the case of polyethers, the first 4 points of these specifications can be met, but the final one is a problem. This is because, when a paraffin is replaced, weight for weight, with a polyether having the same boiling point, diffusion kinetics that can be up to twice as fast are observed.

In order to solve this last problem, the applicant has found that polymeric viscosifying agents can be advantageously used to control the diffusion kinetics without changing the other performance qualities according to the specifications.

DESCRIPTION OF THE INVENTION

Thus, the present invention describes an animal pheromone formulation characterized in that comprises:
a) a solvent of polyether or polyester type,
b) an animal pheromone,
c) a polymeric viscosifying agent.

Such formulations of semiochemical compounds for mammals prove to be particularly effective in wick diffusers for controlling the diffusion of several semiochemicals having different volatilities over long periods of time and independently of the temperature and humidity conditions.

According to one particular embodiment, the formulation comprises between 85 and 98% by weight of solvent of polyether or polyester type.

According to one particular embodiment, the formulation comprises from 0.1 to 15% by weight of animal pheromone.

According to one particular embodiment, the formulation comprises between 0.1 and 10% by weight of polymeric viscosifying agent.

According to a more particular embodiment, it involves formulations of animal pheromones, in particular for a wick diffuser, characterized in that they contain:

from 85 to 99% of a solvent of polyether or polyester type,
from 1 to 15% of animal pheromone, and
from 0.1 to 10% of polymeric viscosifying agent.

According to the invention, the percentages are expressed by weight of the total weight of the formulation, unless otherwise indicated.

Preferably, the solvent according to the invention is a polyether having a boiling point of greater than 200° C., and more preferentially the solvent is Dowanol™ TPnB or a chemical equivalent of another brand, tetraoxaundecane or 2 ethylhexylal.

More particularly, the viscosifying polymers used for these formulations are polymers or copolymers having an average molecular weight of greater than 10 000 g/mol and less than 100 000 g/mol. They in particular have low solubility in polyethers and contain acrylic and/or methacrylic units.

By the term "low-solubility polymer" the applicant intends to mean a polymer of which the solubility in the polyether does not exceed 0.5% at an ambient temperature of 20° C., but which can be more than 5% soluble at a temperature greater than 50° C.

Even more preferentially, the polymeric viscosifying agents are block copolymers containing an acrylate block and at least one methyl methacrylate block, preferably two. In particular, the viscosifying polymers can be even more preferentially chosen from the polymers of the Nanostrength™ brand developed by the company Arkema.

The formulations are also characterized in that they contain between 0.1% and 10% of pheromone, preferably between 0.5% and 5% by weight.

The pheromones that can be used in the invention are all mammalian pheromones. Preferentially, the pheromones are mammalian appeasing pheromones. They are in particular mammalian pheromones comprising a fatty chain, and even more particularly mammalian pheromones of fatty acid or fatty ester type chosen from the group consisting of fatty acids having 7 to 20 carbon atoms, fatty diacids such as pimelic acid or azelaic acid, alkyl glycerols (AKG) or derivatives thereof and 2-methyl-2-butenal.

Among these animal pheromones, mention may for example be made of: appeasing pheromones, such as the F3 fraction (facial pheromone) for cats, obtained according to patent EP0724832B1, or pheromones which mimic natural pheromones of nursing females, as described in WO 9937297 (for example sold in products such as Adaptil®, Suilence®), Feliway™ Friends containing the CAP (Cat Appeasing Pheromone) fraction, or compositions containing alkyl glycerols, such as erucyl alcohol, chimyl alcohol or acetals thereof obtained with 2-methyl-2-butenal.

Moreover, those skilled in the art will add any stabilizer, such as in particular antioxidants or anti-UV agents, which makes it possible in particular to preserve the integrity of the mixture throughout the time of use according to what is already widely described in the prior art.

The antioxidants may be chosen from the group consisting of vitamin E, butylated hydroxyanisole (BHA), butylated hydroxytoluene (BHT), used alone or as a mixture. These antioxidants protect the semiochemical substance against degradation and can be added in amounts, as percent by weight of the composition, ranging from approximately 0.1% to approximately 3%, particularly between 0.5 and 2%.

The anti-UV additives may be chosen from the group consisting of beta-carotene, p-aminobenzoic acid, hindered amines and hindered alkoxyamines used alone or as a mixture. These anti-UV agents protect the semiochemicals against degradation by light and can be added in amounts, as percent by weight of the composition, ranging from approximately 0.1% to approximately 3%, particularly between 0.5 and 2%.

The present invention also relates to a wick diffuser containing the formulation according to the present invention as described above.

Such formulations are advantageously used in wick diffusers with the aim of appeasing animals in living areas or for livestock.

EXAMPLES

Example 1: Material and Method of Manufacture

The diffusers consist of commercial PET bottles with a volume of 50 ml, that are stoppered with a polyamide or polypropylene wick holder.

The wicks used are commercial wicks made of wood composite that can be purchased from manufacturers such as Shangai Prima.

The additive polymers are NanoStrength block copolymers manufactured by the company Arkema and which are self-assembled block copolymers that structure on a nanometric scale. The commercial references of these products are: nano Strength™ M22 and M53.

The Dowanol™ TpnB solvent is purchased from the company Unipex, the distributor of these products in Europe. Its official name is 1-[(2-butoxy-1-methylethoxy)-1-methylethoxy]-2-propanol. This solvent does not present any danger to humans or the environment.

The cold and hot solubilities of these polymers in Dowanol™ TpnB are given in the following table:

|  | M22 | M53 |
| --- | --- | --- |
| Solubility at 20° C. (% by weight) | 0.012% | 0.029% |
| Hot solubility (100° C.) (% by weight) | >5% | >7% |

The M22 and M53 polymers thus correspond to the definition of the invention. They have the particularity of not being cold soluble (therefore of not viscosifying the solution under cold conditions, but only of viscosifying the solution under hot conditions).

Example 2

The formulations of the following examples are produced according to the following process:

The solution of Dowanol™ TpnB containing the pheromone is prepared in a jacketed stirred reactor.

This mixture is heated to 70° C. and then the desired amount of additive M53 polymer is added and maintained with stirring at 70° C. until complete dissolution of the polymer. The temperature of the mixture is then brought back to ambient temperature.

The bottles are then filled to an amount of 48 g per bottle and then stoppered with the wick carrier, the wick and the screw cap.

A commercial Feliway™ bottle is used as reference.

The following table summarizes the mixtures that were produced according to the invention under these conditions:

| Example | Reference | 2A | 2B | 2C | 2D | 2E | 2F (control) |
|---|---|---|---|---|---|---|---|
| Animal | Chat | Cat | Cat | Cat | Dog | Horse | — |
| Solution (ml) | 48 | 48 | 48 | 48 | 48 | 48 | 48 |
| Pheromone (g) | 0.972 | 1 | 1 | 1 | 1 | 1 | 1 |
| Solvent (nature) | Paraffin | TPnB | TPnB | TPnB | TPnB | TPnB | TPnB |
| Solvent (g) | 45.1 | 43.6 | 43.6 | 43.6 | 43.6 | 43.6 | 43.6 |
| M53 (g) | 0 | 0.22 | 0.044 | 0.088 | 0.22 | 0.22 | 0 |

Example 3: Comparison of the Evaporation Kinetics as a Function of the Composition in Ventilated Ovens In order to compare the evaporation kinetics, all the samples are on a socket board so that all the samples evaporate under the same conditions. The ambient temperature of the room in which the experiment is carried out is between 21 and 23° C.

The experiment is repeated 10 times so as to have a statistical analysis of the evaporation times. The weights of each bottle are then evaluated and the amount evaporated from the beginning of the experiment is deduced therefrom. The half-lifetimes and times corresponding to 90% diffusion are reported in the following table.

|  | Reference | 2A | 2B | 2C | 2F |
|---|---|---|---|---|---|
| T50 (d) | 15 (+/−1) | 21 (+/−2) | 12 (+/−1) | 16 (+/−1) | 9 (+/−1) |
| T90 (d) | 28 (+/−5) | 39 (+/−8) | 23 (+/−4) | 30 (+/−4) | 18 (+/−3) |

The results illustrate the following phenomena:

The kinetics of formulation 2F are 1.6 times faster than those of the reference. This illustrates the more polar nature of Dowanol™ TpnB compared to the solvent used in the reference. Indeed, the kinetics are mainly linked to the elution of the formulation in the composite wick.

The diffusion time in the formulations 2F, 2B, 2C and 2A increases and this increase is linearly dependent on the amount of polymer in the formulas.

It is noted that the amount of 0.2% of M53 polymer enables the diffusion kinetics to be made equivalent to those of the reference.

The invention claimed is:
1. An animal pheromone formulation, wherein it comprises:
    a solvent of polyether type,
    an animal pheromone, and
    a polymeric viscosifying agent.
2. The formulation as claimed in claim 1, wherein it contains between 85 and 98% by weight of solvent.
3. The formulation as claimed in claim 1, wherein the solvent has a boiling point of greater than 200° C.
4. The formulation as claimed in claim 1, wherein it contains between 0.1 and 10%, by weight of animal pheromone.
5. The formulation as claimed in claim 1, wherein it contains between 0.1 and 10% by weight of polymeric viscosifying agent.
6. The formulation as claimed in claim 1, wherein the formulation contains between 0.1 and 10% by weight of polymeric viscosifying agent and said polymeric viscosifying agent is a polymer having a molecular weight of between 10 000 g/mol and 100 000 g/mol.
7. The formulation as claimed in claim 1, wherein the formulation contains between 0.1 and 10% by weight of polymeric viscosifying agent and the polymeric viscosifying agent is a copolymer containing acrylic units and methacrylic units.
8. The formulation as claimed in claim 1, wherein the formulation contains between 0.1 and 10% by weight of polymeric viscosifying agent and the polymer is a block copolymer containing an acrylic block and at least one methyl methacrylic block.
9. The formulation as claimed in claim 1, wherein the pheromones are mammalian appeasing pheromones.
10. The formulation as claimed in claim 1, wherein the solvent is a polyether, preferably chosen from 1-[(2-butoxy-1-methylethoxy)-1-methylethoxy]-2-propanol, 2-ethylhexylal, tetraoxaundecane and a mixture thereof.
11. A wick diffuser containing the formulation as claimed in claim 1.

* * * * *

UNITED STATES PATENT AND TRADEMARK OFFICE
CERTIFICATE OF CORRECTION

| | | |
|---|---|---|
| PATENT NO. | : 11,529,418 B2 | Page 1 of 1 |
| APPLICATION NO. | : 16/956763 | |
| DATED | : December 20, 2022 | |
| INVENTOR(S) | : Olivier Guerret and Samuel Dufour | |

It is certified that error appears in the above-identified patent and that said Letters Patent is hereby corrected as shown below:

In the Claims

Column 6, Claim 10, Line 43, delete ", preferably".

Signed and Sealed this
Fifteenth Day of August, 2023

Katherine Kelly Vidal
*Director of the United States Patent and Trademark Office*